United States Patent [19]

Vegh et al.

[11] 4,243,596
[45] Jan. 6, 1981

[54] (5-NITRO-2-FURYL)VINYLENE-2-TRIME-THYLAMMONIUM BROMIDE AND METHOD OF PREPARING SAME

[75] Inventors: Daniel Vegh; Jaroslav Kovac, both of Bratislava, Czechoslovakia

[73] Assignee: Rektorat Slovenskej vysokej skoly technickej, Bratislava, Czechoslovakia

[21] Appl. No.: 21,831

[22] Filed: Mar. 19, 1979

Related U.S. Application Data

[63] Continuation-in-part of Ser. No. 860,977, Dec. 15, 1977, abandoned.

[30] Foreign Application Priority Data

Dec. 15, 1976 [CS] Czechoslovakia ............... 8191-76

[51] Int. Cl.$^3$ ............................................. C07D 307/73
[52] U.S. Cl. .................................................. 260/347.7
[58] Field of Search ...................... 260/347.7, 567.6 M

[56] References Cited

U.S. PATENT DOCUMENTS 3,164,607  1/1965  Lednicer ................. 260/567.6 M X
3,347,874  10/1967  Eloy ........................... 260/347.7
3,836,528  9/1974  Minami et al. ............ 260/347.7 X
4,046,781  9/1977  Yu .............................. 260/347.7

OTHER PUBLICATIONS

Patai, The Chemistry of the Amino Group, Interscience Publishers, New York, (1968), p. 45.

*Primary Examiner*—Richard Raymond

[57] ABSTRACT (5-Nitro-2-furyl)vinylene-2-trimethylammonium bromide having the formula

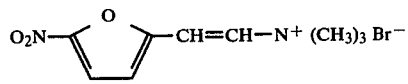

is suitable as a starting raw material for a plurality of syntheses of 5-nitro-2-furyl ethylene compounds possessing an antibacterial effect. The method of preparing the bromide involves reacting 1-(5-nitro-2-furyl)-2-bromoethylene with trimethylamine in an organic solvent medium at a temperature of from −10° to +50° C.

1 Claim, No Drawings

(5-NITRO-2-FURYL)VINYLENE-2-TRIMETHYLAMMONIUM BROMIDE AND METHOD OF PREPARING SAME

This application is a continuation-in-part of copending application, Ser. No. 860,977, filed Dec. 15, 1977, now abandoned.

This invention relates to 5-nitro-2-furylvinyleneammonium salts having an aliphatic tertiary amine, and to a process for the preparation thereof. More specifically, the present invention relates to (5-nitro-2-furyl)vinylene-2-trimethylammonium bromide and to a method for the preparation thereof.

Heretofore workers in the art have sought new routes for preparing antibacterially-effective 5-nitro-2-furyl ethylene compounds. In accordance with the present invention, this end is attained by means of the noted vinylene ammonium salt.

The method employed for this purpose involves reacting 1-(5-nitro-2-furyl)-2-bromoethylene with trimethylamine in an organic solvent or blends thereof at a temperature ranging from −10° to 50° C. Solvents found suitable for this purpose include benzene, toluene, xylene, ether, acetone, dimethylformamide, aliphatic alcohols having 1-4 carbon atoms, dioxane, tetrahydrofuran, chloroform, tetrachloromethane and the like. This procedure for preparing (5-nitro-2-furyl)vinylene-2-triethylammonium bromide has been found economically attractive and, from a procedural standpoint, is simple.

The reaction which occurs is shown in equation (1) as follows:

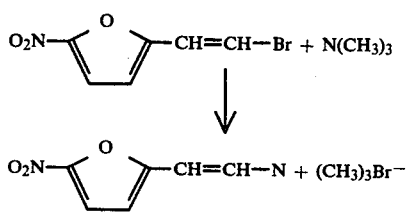

With the preparation of this compound, it has been found possible to prepare a wide variety of oxygen, sulfur, nitrogen and phosphorous derivatives of 5-nitro-2-vinyl furan compounds which are biologically active. Additionally, organo metallic derivatives thereof have been prepared. These compounds are of the general formula

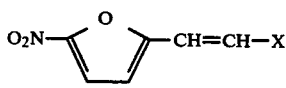

wherein X is selected from among oxygen, sulfur, nitrogen, phosphorous, mercury, tin and boron.

Typical 5-nitro-2-furylethylene compounds may be obtained, as for example, by reaction of 0.01 mole of (5-nitro-2-furyl)vinylene-2-trimethyl ammonium bromide dissolved in 20–25 milliliters of water with 0.011 moles of a substituted sodium or potassium arylthiophenoxide in 25 milliliters of water. The precipitate resulting from this reaction may then be filtered off and purified by cyrstallization or chromotographically on a silica gel column to yield the following sulfur derivative, (A), of 5-nitro-2-furylethylene:

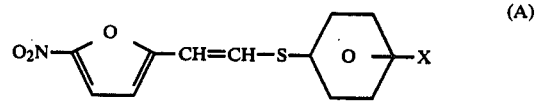

where X is as defined above.

Oxidation of (A) in acetic acid and hydrogen peroxide yields compound (B) below.

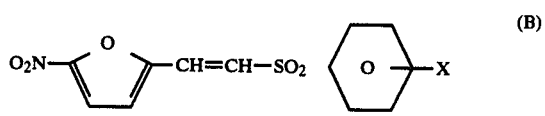

wherein X is as defined above.

It will be appreciated that compound (B) may also be obtained by reaction of (5-nitro-2-furyl)vinylene-2-trimethylammonium bromide with a substituted arylsulfinate of the general formula

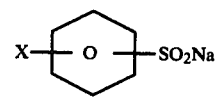

wherein X is as defined above. Each of the compounds described, (A) and (B), evidences significant antibacterial activity against both gram-positive and gram-negative bacterial in a concentration ranging from 1.125 to 50 gamma. Compound (B) also evidenced an outstanding anticoccidal activity.

Oxygen derivatives of 5-nitro-2-furylethylene may be prepared, for example, by reaction of 0.01 mole of (5-nitro-2-furyl)vinylene 2-trimethylammonium bromide dissolved in 25 milliliters of water with 0.011 mole of substituted sodium or potassium phenoxide in 25 milliliters of water. The resultant precipitate may then be crystallized to obtain a 60 to 95% yield of compound (C) below.

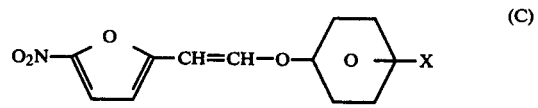

wherein X is as defined above. This family of compounds evidences a strong antibacterial activity against both gram-positive and gram-negative bacteria in a concentration ranging from 3 to 50 grams.

The following examples are given by way of illustration. It will be understood, however, that such illustration is not restrictive in nature.

EXAMPLE 1

To a solution of 11 g (0.05 mole) 1-(5-nitro-2-furyl)-2-bromoethylene in 150 ml benzene there was added dry trimethylamine at a temperature of from 0° to 15° C. the reaction mixture was then allowed to stand for several hours at room temperature. Precipitated crystals of (5-nitro-2-furyl)vinylene-2-trimethylammonium bromide were sucked off and washed with ether. The melting point of the bromide varied between 175° and 185° C. The excluded crystalline substance was recrystallized out of a methanol/ether mixture; its melting point was 178° to 181° C.; the yield was 12 g, i.e., 87%.

EXAMPLE 2

A solution of 3 g (0.05 mole) trimethylamine was added dropwise to a solution of 11 g (0.05 mole) 1-(5-nitro-2-furyl)-2-bromoethylene in 150 ml ether at 0° C. under continuous agitation. The reaction mixture was then allowed to stand for 10 hours at the working temperature and for 5 hours at room temperature. There was obtained 13 g of a yellowbrown crystalline substance having a melting point of from 170° to 195° C., which substance was sucked off and washed with ether. The recrystallization was carried out in the manner described in Example 1. The yield was 12.4 g (5-nitro-2-furyl)vinylene-2-trimethylammonium bromide (i.e., 89%).

(5-Nitro-2-furyl)vinylene-2-trimethylammonium bromide is a compound having the formula

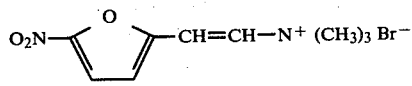

The empirical formula of this compound is $C_9H_{13}BrN_2O_3$; molecular weight 277.12; melting point 178° to 181° C. Its elemental analysis is:

|  | %C | %H | %N | %Br |
|---|---|---|---|---|
| calculated percentage | 39.00 | 4.73 | 10.11 | 17.32 |
| effective percentage | 38.89 | 4.75 | 10.15 | 17.45 |

The structure of (5-nitro-2-furyl)vinylene-2-trimethylammonium bromide was proved by spectral analyses, and more particularly by IR, UV and $^1$H-NMR spectroscopy.

UV spectra were measured by means of a spectrophotometer (SPECORD UV VIS, Carl Zeiss, Jena). As solvents there were used ethanol and water. The substance exhibited the following absorption bands:

| ethanol | water |
|---|---|
| max. = 225 nm 10 g = 4.11 | max. = 227 nm 10 g = 4.21 |
| max. = 257 nm 10 g = 3.65 | max. = 259 nm 10 g = 3.69 |
| max. = 333 nm 10 g = 4.17 | max. = 346 nm 10 g = 4.18 |

IR spectra were measured by means of a spectrophotometer (UR-20 Carl Zeiss, Jena) by using the KBr technique.

The IR spectrum exhibited the following characteristic bands:

$3030\ cm^{-1}$; $1672\ cm^{-1}$; $1584\ cm^{-1}$; $1532\ cm^{-1}$; $1485\ cm^{-1}$; $1470\ cm^{-1}$; $1407\ cm^{-1}$; $1360\ cm^{-1}$; $1310\ cm^{-1}$; $1260\ cm^{-1}$; $1245\ cm^{-1}$; $1208\ cm^{-1}$; $1042\ cm^{-1}$; $1030\ cm^{-1}$; $1010\ cm^{-1}$; and $980\ cm^{-1}$; $945\ cm^{-1}$; $925\ cm^{-1}$.

$^1$H-NMR spectrum was obtained by measuring the substance in dimethyl sulphoxide, trimethylsilane being used as inert standard.

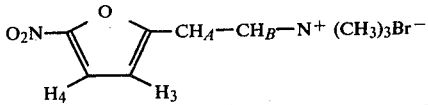

| $H_3$ doublet 7.05 |
| $H_4$ doublet 7.76 |
| $H_A$ singlet 7.38 |
| $H_B$ singlet 7.36 |

(5-Nitro-2-furyl)vinylene-2-trimethylammonium bromide according to the present invention is a substance which is easily soluble in water and readily reacts with aqueous solutions of other compounds. It constitutes a starting raw material for a plurality of syntheses of 5-nitro-2-furyl ethylene compounds possessing an antibacterial effect. The use of (5-nitro-2-furyl)vinylene-2-trimethylammonium bromide of the invention substantially simplifies such syntheses and makes them inexpensive.

Further evidence of reactions of the described compounds is shown in Vegh, Kovac and Povazanec, *Preparation and Reactions of Z and E Isomers of 5-Nitro-2-Furylvinyl Azide*, 43 Coll. Czech. Chem. Comm. (1978), 3404–3408, which is incorporated herein by reference. A copy of said publication is attached.

Although the invention is described with reference to a plurality of examples thereof, it is to be expressly understood that the invention disclosed herein is not limited in any way to such examples, but is to be construed in light of the appended claims.

What is claimed is:

1. (5-Nitro-2-furyl)vinylene-2-trimethylammonium bromide having the formula

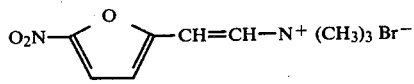

* * * * *